(12) United States Patent
Cole et al.

(10) Patent No.: US 7,155,988 B2
(45) Date of Patent: Jan. 2, 2007

(54) DUAL AIR PARTICLE SAMPLE CASSETTE

(75) Inventors: Mark A. Cole, Santa Ana, CA (US); Thomas J. Johnston, Santa Ana, CA (US)

(73) Assignee: Innovative Sampling Solutions, Inc., Garden Grove, CA (US)

( * ) Notice: Subject to any disclaimer, the term of this patent is extended or adjusted under 35 U.S.C. 154(b) by 171 days.

(21) Appl. No.: 10/875,095

(22) Filed: Jun. 22, 2004

(65) Prior Publication Data
US 2005/0279182 A1 Dec. 22, 2005

(51) Int. Cl.
*G01N 1/00* (2006.01)
(52) U.S. Cl. ............................................. 73/863.22
(58) Field of Classification Search ............ 73/863.21, 73/863.22, 863.23, 863.25, 28.04, 28.05, 73/28.06, 863.33, 863.31
See application file for complete search history.

(56) References Cited

U.S. PATENT DOCUMENTS

| | | | | |
|---|---|---|---|---|
| 3,489,012 A | * | 1/1970 | Niskin | 73/863.31 |
| 3,686,835 A | * | 8/1972 | Strange et al. | 96/417 |
| 3,698,161 A | | 10/1972 | Brixius et al. | 55/493 |
| 3,884,081 A | * | 5/1975 | Griffith | 73/863.31 |
| 3,970,428 A | * | 7/1976 | Barringer | 73/863.22 |
| 4,133,202 A | | 1/1979 | Marple | 73/28 |
| 4,350,037 A | * | 9/1982 | Higham | 73/23.39 |
| 4,827,779 A | | 5/1989 | Marple et al. | 73/863.22 |
| 5,553,507 A | | 9/1996 | Basch et al. | 73/863.01 |
| 5,693,895 A | | 12/1997 | Baxter | 73/863.22 |
| 5,702,506 A | | 12/1997 | Shih et al. | 95/287 |
| D422,071 S | | 3/2000 | Miller et al. | D23/365 |
| 6,217,636 B1 | * | 4/2001 | McFarland | 95/216 |
| 6,342,388 B1 | | 1/2002 | Van Den Wildenberg | 435/287.1 |
| 6,463,814 B1 | * | 10/2002 | Letarte et al. | 73/863.22 |
| 6,565,638 B1 | | 5/2003 | Sugita et al. | 96/413 |
| 2003/0075048 A1 | | 4/2003 | Jordan et al. | 95/285 |

* cited by examiner

*Primary Examiner*—Robert Raevis
(74) *Attorney, Agent, or Firm*—Stout, Uxa, Buyan & Mullins, LLP; Donald E. Stout

(57) ABSTRACT

An air particle sample cassette enables concurrent or sequential collection of air particle samples. The dual air particle sample cassette has top and bottom covers that fit together to provide an airtight seal between them. The airtight seal may be provided by adhesive or otherwise. However, a close fit between the two also aids in obtaining an airtight seal. The top cover has tapering inlets circumscribed by channels. The inlets taper to create increased air speed at the exit slit of the inlets. The inlets have rounded tops for greater collection of air and the circumscribing channels provide means by which plastic caps or otherwise may be used to protect the inlets from collecting air until desired. The sample plate or collecting slide is fitted to the bottom of the top cover and obstructs the direct flow of air to the exit port. The collecting slide is protected from contact with other cassette elements by spacers or sidewalls which generally leave the corners of the bottom cover open. The exit port enables the common application of vacuum pressure to draw air through the inlets. Different inlet characteristics or air speeds may serve to enable selection of size of the particle sampled. Filter elements may also be introduced upstream of the inlets to further select sample particle size.

22 Claims, 5 Drawing Sheets

DUAL AIR PARTICLE SAMPLE CASSETTE

COPYRIGHT AUTHORIZATION

Portions of the disclosure of this patent document may contain material which is subject to copyright and/or mask work protection. The copyright and/or mask work owner has no objection to the facsimile reproduction by anyone of the patent document or the patent disclosure, as it appears in the Patent and Trademark Office patent file or records, but otherwise reserves all copyright and/or mask work rights whatsoever.

BACKGROUND OF THE INVENTION

1. Field of the Invention

This invention relates to air particle sampling cassettes and devices, and more particularly to a dual air particle sample cassette that enables one or more samples of air to be taken at a time by the same vacuum sources.

2. Description of the Related Art

Air sampling has become an important aspect of safety and health concerns due to the rise of the present day industrial economy. Additionally, certain health aspects of individuals are better addressed when the pollen and/or particulate count of the surrounding area is known.

With respect to industrial processes and the like, chemical processes are often used in industries that produce substances that are generally not found in nature. Many of these are toxic and must be monitored in order to prevent injury, sickness, disease, or even death in individuals that might be exposed to such substances. Some of these substances are very potent and act very quickly while others require longer periods of time in order to have their deleterious effect. By monitoring or sampling the air, quantitative evaluations can be made upon such substances in the air.

With respect to people who have allergies, the pollen, mold, dust, and other particulates becomes important as their health is directly (and usually adversely) affected by the increase in such substances. By providing means by which such particulates can be detected, an individual allergic (or a community thereof) is better prepared to address the environmental conditions.

Other uses and applications for air samplers and the information delivered by them arise in a variety of circumstances. Certain biological, botanical, and other endeavors may benefit from an understanding of the air quality in certain areas. To this extent and otherwise, air sampling systems have arisen in the art to provide means by which quantitative information regarding air quality can be obtained by direct sampling of the air.

As set forth in U.S. Pat. No. 5,693,895 issued to Baxter on Dec. 2, 1997 for a Versatile Airborne Particle Impaction Sampler, obtaining accurate samples of airborne particles such as fibers, pollen, mold spores, insect parts and other bioaerosols is necessary or desirable for a number of different purposes. Environmental professionals have a need to determine the presence and quantity of deleterious particles such as asbestos fibers in the air. Aero-biologists and allergists need to identify and quantify airborne pollen and mold spore concentrations for patient diagnosis. Epidemiologists are concerned with particles carrying bacteria, such as that responsible for Legionnaire's Disease, in air-conditioning systems and the like.

An increasing need for more versatile, convenient and effective apparatus for sampling airborne particles has developed in such areas as environmental air quality monitoring, fire and flood restoration, and industrial and occupational monitoring.

Filter sampling has long been used for particle and fiber analysis. Air is drawn through a micro porous filter of the sort marketed by Millipore, Nuclepore and other companies. The filter is then examined under a microscope to determine the type and concentration of particles trapped on the filter media.

While effective for some purposes, filter sampling requires long sampling times to obtain reliable detection limits. The large filter areas require slow, careful examination by the microscopist performing the analysis. Relatively large filter areas, typically about 385 to 900 $mm^2$, are normally required to balance high sample flow rates, required velocity and resulting back pressures. Large particles such as pollen often do not remain attached to the filter, separating there from during transportation and handling. Further, special stains and refractive index liquids required to assist in particle identification are often incompatible with the filter media.

Slit or impact samplers, which direct air at relatively high velocity through a narrow rectangular slit against a tacky material, have a number of advantages over filter sampling. A sample sufficient for analysis can be obtained in minutes rather than hours, the area to be examined is much smaller (approximately 16 $mm^2$) than the areas provided with filters and the tacky nature of the material used to collect the sample will retain large particles better than filters. Present slit type samplers are assembled in a housing containing a vacuum pump, a holder for a slide coated with a tacky material, such as a suitable grease, with a narrow rectangular slot in the housing adjacent to the tacky surface.

These devices can only be used in an upright or fixed position and cannot be easily used in confined or restricted spaces such as ventilation ducts because of their relatively large size. Electricity to power the vacuum pump must also be run to the sampling site, or a battery power source in the housing must be provided which further increases the bulk of the unit. These units are not weatherproof and are difficult to use in moist or exposed areas. Dust contamination can build up inside the case resulting in cross contamination of sample slides and will require regular and extensive cleaning between sample collection episodes. Further, slit geometry in prior collectors is such as to collect the undesired less than about 2 μm particles, making examination and analysis more difficult.

Upon completion of sampling, the slides must be removed from the sampling device, packaged and shipped for analysis. Users must have specialized knowledge of sampling, decontamination, shipping and analysis procedures. Still, the opportunity for contamination, either inadvertent or intentional, is great.

With patients in hospitals, allergic persons while sleeping, workers in confined environments, etc. often have need for sampling near their faces to determine their actual exposure to allergens, toxic materials, etc. The large sampling devices of the prior art are very inconvenient for such uses, in particular where the person is mobile, because of their lack of easy portability.

Prior attempts have been made in the art with respect to sample cells and cassettes for air sampling systems and otherwise. Brief descriptions of such prior attempts are set forth below. While the descriptions are believed to be accurate, no admission is made by them regarding their subject matter which is solely defined by the patent or reference involved.

Typical of prior particle collection devices are those described by Berger in U.S. Pat. No. 4,725,294 and Leith in U.S. Pat. No. 5,304,125. The Berger device uses a single, round nozzle that will produce a circular, gradually decreasing spot of collected particles that is much more difficult to analyze than a narrow line of particles and will tend to collect sub-micron particles that obscure the larger which are to be analyzed. Leith discloses a device using four spaced slits that are simple slots in a thin plate, which will not discriminate between larger particles of interest and sub-micron particles that are not of interest.

The Baxter U.S. Pat. No. 5,693,895 discloses a single collector having a slide that is supported by the bottom ledge of the cell base.

The Marple et al. U.S. Pat. No. 4,827,779 discloses a personal air sampling impactor having a single vacuum source, multiple inlets, and in a separate embodiment, separate collection surfaces on the impactor plate.

The Marple U.S. Pat. No. 4,133,202 teaches a single stage impactor for sampling breathable aerosol particles having a nozzle plate with multiple different sized nozzles for allowing different sized particles through and an impactor unit with a plurality of particle collecting surfaces.

The Basch et al. U.S. Pat. No. 5,553,507 shows an airborne particulate sampling monitor having multiple intakes, each with its own filter unit, and a single vacuum source. The Shih et al. U.S. Pat. No. 5,702,506 teaches an aerosol size selecting sampling device having multiple inlets with pre-filters and a single vacuum source.

Van Den Wildenberg U.S. Pat. No. 6,342,388 discloses an apparatus for collecting airborne bacteria through impaction having multiple inlets and a single vacuum source.

The Sugita et al. U.S. Pat. No. 6,565,638 discloses a device for collecting air-borne micro-organisms having multiple nozzle openings and a single vacuum source.

The Jordan, Sr. et al. U.S. Patent Application Publication No. 2003/0075048 discloses a particle collection unit for separating particulate matter from a gas flow having an adhesive collecting member.

The Brixius et al. U.S. Pat. No. 3,898,161 discloses an air filtration device having a color-coded filter. Refer to column 4, lines 10–12.

The Miller et al. U.S. Pat. No. Des. 422,071—illustrates a partitioned filter element.

The Ayers published international application no. WO 03/002981—teaches a device for collecting and measuring particulate matter from a stream of air using two or more inlets each being selective as to the size of the particle able to pass through the inlet.

Despite the development of prior devices, the art may still be improved by a dual or multiple inlet air particle sample cassette that provides convenient means by which air may be sampled.

SUMMARY OF THE INVENTION

In view of the foregoing disadvantages inherent in the known types of air sampling devices now known in the prior art as well as the advantages of furthering the art with respect to such air sampling systems, the present invention provides a new air particle sample cassette that provides at least two inlets such that air samples can be taken concurrently, sequentially, episodically, or otherwise by means of a disposable or reusable air sample cassette.

The general purpose of the present invention subsequently described in greater detail below is to provide an air sampling system that enables multiple samples to be taken either at the same time or at different times as multiple inlets transmitting air to isolated chambers provide separate and independent air particle sampling systems in a tandem or multiple package for better, more consistent, or more convenient air particle sampling, the cassette not anticipated, rendered obvious, suggested, taught, or even implied by any of the prior art air sampling systems or devices, either alone or in any combination thereof.

In the present invention, the dual air particle sample cassette has a top half and a bottom half which fit together to provide a sealed enclosure in which air samples are obtained. The top half of the air sample cassette has a pair of inlets of generally square or rectangular in nature that taper into corresponding narrow slots so that a volume of air is rapidly accelerated to a significantly high velocity by means of the Venturi effect or otherwise. This high velocity air carries any particulate materials with it which are also subject to acceleration and increased velocity.

An obstructing sample collection plate is present in front of each slit opening in order to obstruct the direct path of the air and particle flow. A sample plate is held in place at the bottom of the top cover and is spaced apart and away from the narrow slit opening. This enables the sample plate to travel with the inlets. The sample plate defines a collection area in front of each narrow slit with each collection area isolated and separate from all other collection areas. The sample plate does not fully enclose the collection area, but a gap at the edge of the collection plate is present between itself and the bottom sidewalls of the top cover to allow the escape of air and any particles not collected by the tacky medium present on the surface of the sample plate. A partition or rib separates the individual collecting areas or chambers of the top cover by contact engagement with the sample plate. Consequently, airflow cannot occur between the areas in front of the slit inlets to the collecting area at the tapered ends of the inlets of the top cover.

The air then travels through this gap and onto the interior of the bottom cover where a nozzle or outlet is subject to vacuum pressure which pulls the air through the cassette and the tapered top inlets of the top cover.

The bottom cover has a well, reservoir, or other receiving area for the bottom portion of the top cover. Ledges, supports, or spacers are present at the sides of the well, but are absent from the corners in order to allow air to pass through or otherwise. The air passing through the sample plate gap travels through and about the enclosed area defined between the top and bottom covers and out the vacuum nozzle.

Legs, support, or spacing elements may be present at the eight corners (4 top, 4 bottom) of the cassette. These legs or supports may enable easy engagement in air sampling system by the cassette.

Generally, one sample plate or collecting slide may be fixed in place onto the top cover with no sample contamination occurring between collection areas as the sampling areas are separated by at least one partition. The inlets may be shaped to efficiently sample different particle sizes, including 5 μm particles and 20 μm and larger particles. The cassette may have two identical inlets as might be used for a 5 μm particle collection or two different nozzles with one for 5 μm and another for 20 μm particle sampling, for example. Only a single exit vacuum port is present in the cassette so that one vacuum source is needed for either concurrent or sequential particle collection.

The sample plate or collecting slide has tacky material on its top facing the narrow slit of the inlet for nonviable particle sampling or the collecting slide may have biocompatible media for viable sampling. Alternatively, one side or collecting area may have tacky material for nonviable particle sampling and the other side may have tacky media for biocompatible for a viable sampling.

When delivered to the customer or user, the inlets may be covered with tamper proof tape and/or removable and/or replaceable cap. The cap may be made of plastic.

The collecting slides sample plate may be coded to correspond with a certain select inlet for permanent sample identification. The collecting slide sample plate may be configured with a filter for sampling both viable and nonviable particles. Additionally, a disposable filter screen may be fitted onto one or more of the inlets to remove debris in the air before it is sampled.

In one embodiment, an air particle sample cassette receives a sample plate to sample air. The cassette has a plurality of inlets with each inlet having a tapering cross section with a first opening wider than a generally oppositely opposed second opening. The second opening leads to a recess that has sidewalls and a rib, the recessed portion capable of receiving a sample plate. The rib separates at least two of the second openings and prevents gas flow between them when the sample plate is positioned over the recess. The sidewalls establish a gap with the sample plate when the sample plate is positioned over the recess. A bottom cover has vacuum aperture and removably encloses the recess. When a vacuum is applied to the vacuum aperture, air is pulled through at least one of the second openings to collide with the sample plate. Matter in the air is collected by the sample plate as it obstructs direct flow of the air to the vacuum aperture and guides the air to the gap.

Upon collecting matter from the air for a certain period of time or otherwise, the sample plate is inspected and/or analyzed for the collected matter. The quality and/or contents of the air can then be analyzed for health, safety, and/or other purposes.

OBJECTS OF THE INVENTION

It is an object of the present invention to provide an air-sampling device.

It is another object of the present invention to provide a dual air particle sample cassette.

It is yet another object of the present invention to provide an air sampling system that has multiple chambers isolated and separated from one another so that independent samples may be taken through selectable operation of the corresponding inlets.

It is yet another object of the present invention to provide a disposable air sample cassette that can take multiple air samples.

It is yet another object of the present invention to provide an air sample cassette for taking multiple air samples either concurrently and simultaneously, or sequentially, or intermittently.

These and other objects and advantages of the present invention will be apparent from a review of the following specification and accompanying drawings. The foregoing objects are some of but a few of the goals sought to be attained by the present invention.

DESCRIPTION OF THE PREFERRED EMBODIMENT(S)

The detailed description set forth below in connection with the appended drawings is intended as a description of presently preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
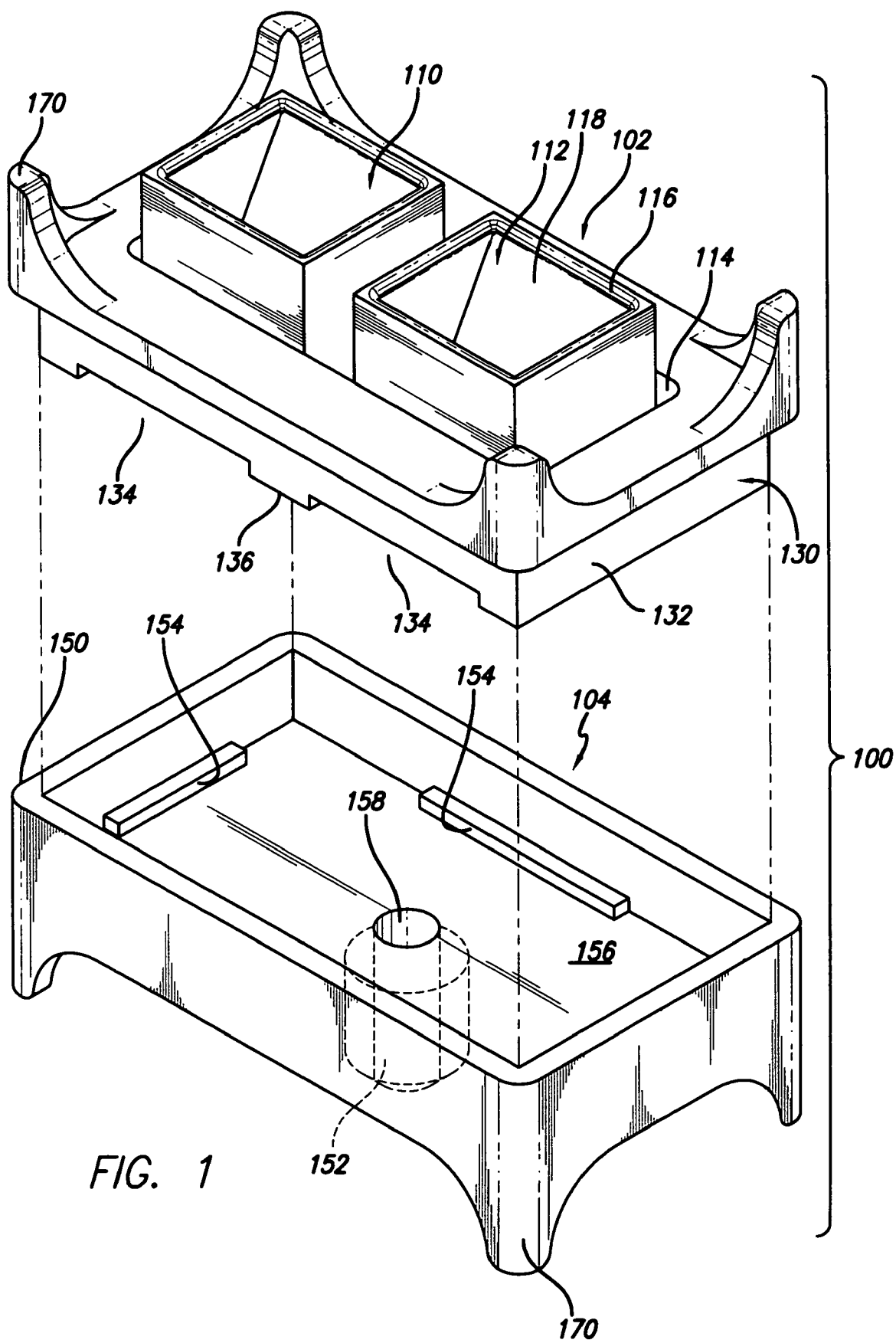
FIG. 1 is an exploded side perspective view of the dual air particle sample cassette of the present invention with the top cover spaced apart and above the bottom cover.
Figure 2:
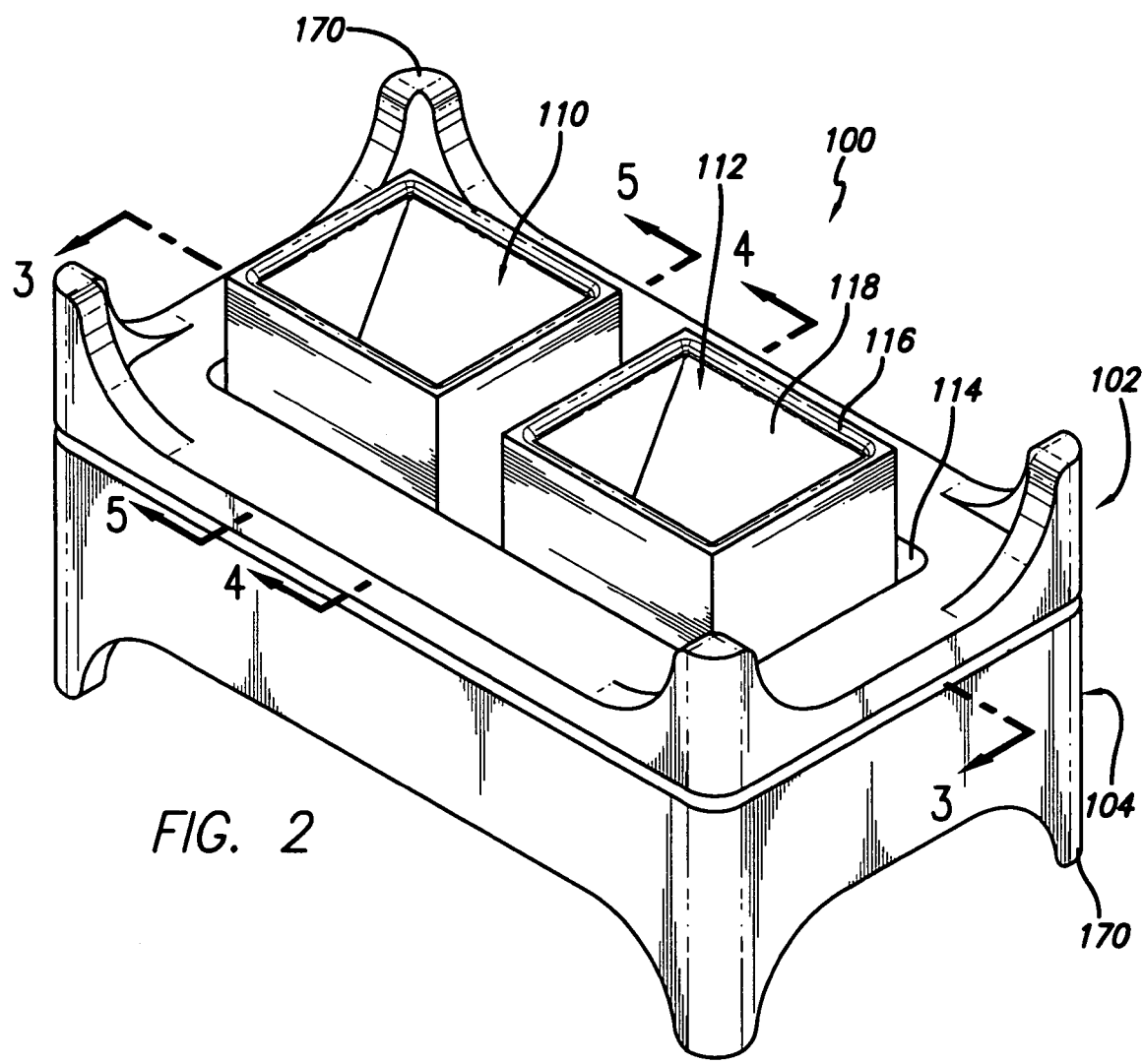
FIG. 2 is a side perspective view of the dual air particle sample cassette of FIG. 1 showing the top and bottom covers fitted together.

Referring to the drawings where like new numerals of reference designate like elements throughout it will be noted that the dual, or multiple, air particle sample cassette 100 of the present invention has a top cover 102 and a bottom cover 104. While FIG. 1 is an exploded of the cassette 100, FIG. 2 shows an assembled portrayal of the cassette 100 with the top 102 and bottom 104 covers are fitted together to generally form an airtight seal that may be secured by tape, adhesive, or otherwise (not shown).

The top cover 102 has inlets 110 and 112. The inlets 110, 112 may be identical or they may be different. By appropriate selection of the difference between the two inlets 110, 112, samples can be taken of different particles. Such differences may include the angle of tapering or the width of the slit at the end of the inlets. Additional characteristics of the inlets may be altered during manufacture or otherwise to achieve performance characteristics that are desirable for the circumstances of the air sampling the cassette 100 is to perform.

The inlets 110, 112 are surrounded by a channel 114 that circumscribes the inlets and passes between them as well. The channel may allow for easier connection to the inlets 110, 112 by caps, covers, conduits, hoses, or otherwise (not shown).

The tops 116 of each of the inlets 110, 112 may be tapered on the interior portion of the inlet but flat on the exterior portion thereof. The tapering of the top 116 of the inlets 110, 112 may provide for greater distribution of the vacuum applied to the cassette 100. The inlets 110, 112 thereby have additional "purchase" on the surrounding air to gather such air from the greater area or cross section. If the interiors 118 were not tapered at the tops 116 thereof, the air would be gathered from a smaller cross section than may be available with tapered tops 116. The inlets 110, 112 only gather air at their top and the air taken in generally has a velocity in the direction of the inlet. By tapering the tops 116, those velocities and directions are made through a wider angle than would be achieved with flat or sharp angular tops 116.

Figure 3:
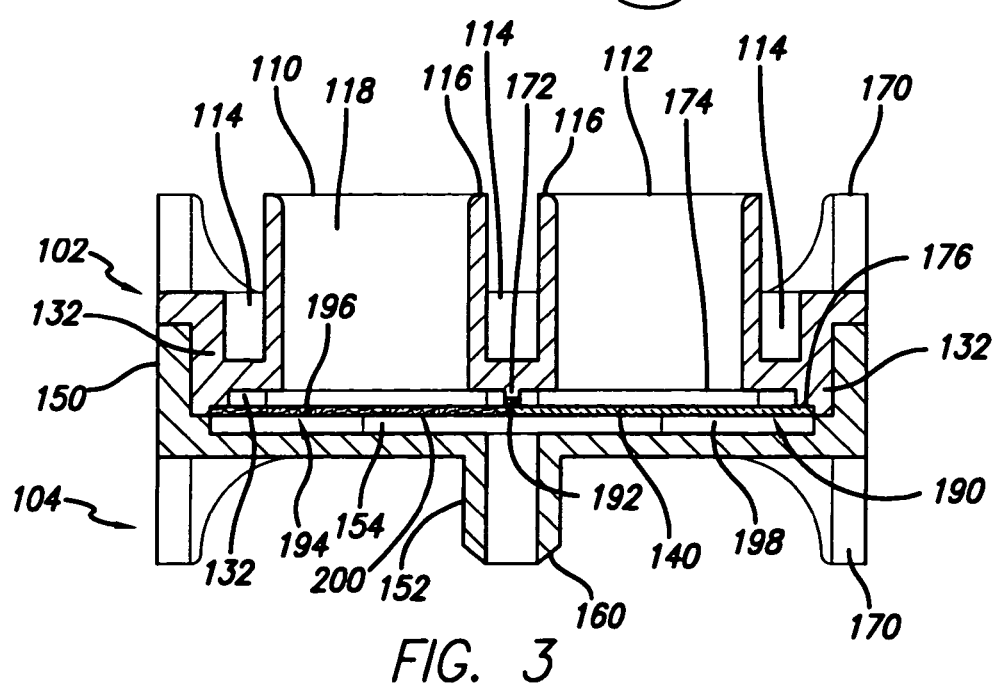
FIG. 3 is a longitudinal cross sectional view of the assembled dual air particle sample cassette of FIG. 2 taken along line 3—3 thereof.
Figure 4:
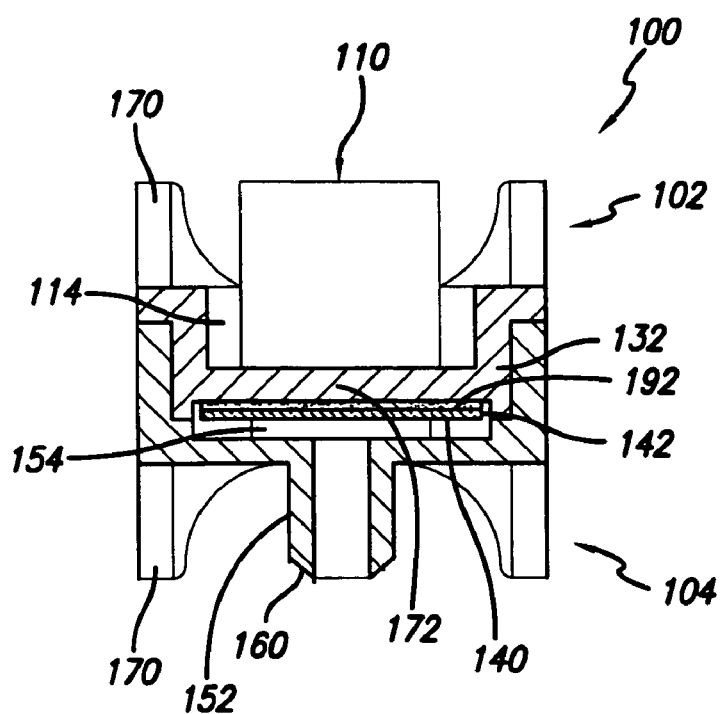
FIG. 4 is a side cross sectional view of the dual air particle sample cassette of FIG. 2 taken along line 4—4 thereof through the channel between the two inlets.
Figure 5:
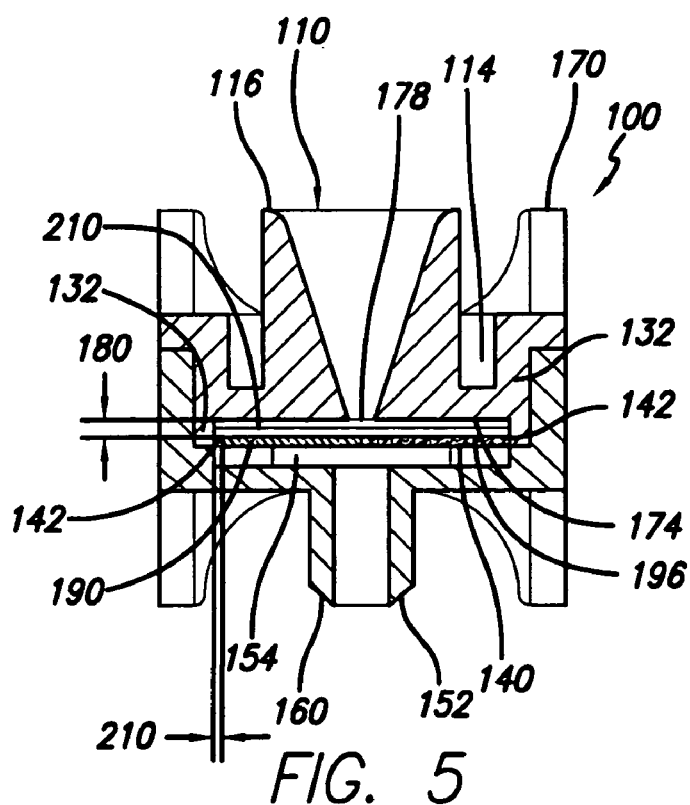
FIG. 5 is a side cross sectional view of the dual air particle sample cassette of FIG. 2 taken along line 5—5 thereof through the left inlet and showing the cross section thereof and its tapering nature.

The bottom portion 130 of the top cover 102 has a circumscribing sidewall 132 which is discontinuous at its bottom-most edge. These discontinuities 134 show as gaps between certain descending elements of the circumscribing sidewall 132. Central posts 136 provide lower support for the top cover 102 and help prevent the bottom cover 104 from engaging the sample plate or collecting slide 140 (FIGS. 3–5). By fitting within the circumscribing sidewall 132 and the central posts 136, the sample plate-collecting slide 140 is recessed within the bottom 130 of the top cover 102.

As shown in FIGS. 4 and 5, the sample plate 140 does not extend completely across the width of the bottom of the top cover 102, although the sample plate preferably does extend the length of the bottom. Instead, a small gap 142 is present between the adjacent sidewall 132 or post 136 and the sample plate 140. This allows air to travel over and across the sample plate 140 before exiting out through the gap 142 and into the bottom cover 104. Without the sample plate, the air coming through the inlets 110, 112 travels straight and onto the bottom cover 104 without having an opportunity to leave any suspended or colloidal particulates on a collection device such as the sample plate 140.

The sample plate 140 requires the accelerated air to impact the sample plate. As the particulates carried by the air have more mass, they have a corresponding greater momentum and inertia. While such particulates will generally have the same speed and velocity as the air emerging from the inlet slot/slit 178, the particulates will not change their direction as quickly as the surrounding air. Instead, the particulates (which are significantly more massive than the surrounding air molecules) will change direction more slowly than the surrounding air when the incoming air encounters the sample plate 140. While the air will have a tendency not to stick to any medium present on the surface of the sample plate 140, the particulates will have a greater tendency to embed themselves or stick to such medium. Not only does the greater momentum of the particulates account for this, but once particulates do contact media, the greater surface area of the particulates allow for greater engagement of such media.

As seen in FIG. 1, the bottom cover 104 generally has a circumscribing outer wall 150 which fits about the circumscribing sidewall 132 of the top cover 102 when the two are fitted together as shown in FIG. 2 or the like. Preferably, generally airtight seal is formed between the inner portion of the circumscribing outer wall 150 of the bottom cover 104 and the outer surface of the circumscribing sidewall 132 with the top cover 102. An airtight seal may also be ensured by adhesive between the two walls 132, 150, airtight tape surrounding the seam between the top and bottom covers 102, 104 or otherwise. It is generally most advantageous to have an airtight seal between the two cover portions 102, 104 as the vacuum that is pulled upon the vacuum nozzle 152 should be transmitted exclusively to the inlets 110, 112 to ensure control over the air sampled by the cassette 100.

The bottom cover 104 has side ledges/supports/spacers 154 at the intersection between the horizontal bottom 156 and the vertical circumscribing outer wall 150. These ledges 154 serve to support the top cover 102 by engaging the circumscribing sidewall 132, the central posts 136, or otherwise. Despite the presence of the circumscribing sidewall 132 and the spacers/ledges 154, an airtight seal is preferable between the top and bottom covers 102, 104. Defined in the bottom 156 of the bottom cover 104 is an aperture 158 generally centrally located in the bottom 156 of the bottom cover 104. The aperture 158 leads to the vacuum nozzle 152 and serves as means by which any vacuum pulled upon the vacuum nozzle 152 is transmitted to the cassette 100 and the inlets 110, 112. As shown in FIGS. 3-5, the vacuum nozzle 152 may be tapered at its end 160 to aid in the application or connection of a vacuum hose or the like.

Both the top and bottom covers 102, 104 have outwardly extending legs 170 which may serve to help assemble and disassemble the cassette 100 as well as providing additional advantages such as protecting the inlets 110, 112 and/or the vacuum nozzle 152 so they do not stand too proud or extend too far outwardly from the central and generally flat portion of the cassette 100.

As shown in FIG. 3, a central rib 172 may be attached to or conjoined with the sample plate 140 by adhesive or otherwise to separate the two or more recessed areas 174 defined by the circumscribing side wall 132 as well as a spacing support ledge 176 circumscribing or otherwise the interior of the bottom 130 of the top cover 102.

The height of the central rib 172 and the spacing support ledge or ledges 176 define the distance between the narrow inlet slot 178 (FIG. 5) and the sample plate/collecting slide 140. This distance between the sample plate 140 and the narrow inlet slot 178 defines how much distance the air travels upon exiting the narrow inlet slit 178. As the path of air travel (FIGS. 3 and 5) is initially towards the sample plate 140 and then to the gap 142, it is most desirable to have the sample plate 140 collect as much particulate matter as is possible before the air exits the associated recessed area 174. Therefore, the distance between the narrow inlet slot 178 and the sample plate 140 should be as great as possible to allow maximum air flow but as small as possible to prevent particles from traveling with the air and not impacting the tacky or adhesive substance(s) present on the top of the sample plate. Correspondingly, the viscosity of the fluid, in this case air, traveling through the narrow inlet slot 178 may be a determining factor as far as the spacing between the narrow inlet slot 178 and the collecting plate 140. In one embodiment, the recessed gap distance 180 may be on the order of 0.5 mm to 15 mm. For low-density gasses, or for high viscosity fluids, other distances may be preferable.

Additionally, in FIG. 5, a gap present between the sample plate 140 and the circumscribing wall 132 may be present to allow passage from the plenum area, or recessed area 174 of the top cover 102 to the lower plenum space 198 of the bottom cover 104. This side gap 210 allows passage of air from the top cover 102 to the bottom cover 104. As is seen in FIG. 5, such a gap is necessary for solid or impermeable sample plates 140 such as glass slides or the like. However, on the right side of FIG. 5, no gap is present for a permeable sample plate 140 such as a filter media or the like. The gap distance may be on the order of 0.5 mm to 2.0 mm or similar. The plenum spaces 174, 198 may have heights on the same order or larger.

Additionally, the width of the narrow inlet slot 178 may be selectably chosen during manufacture or otherwise to determine the speed at which the air passes through the narrow inlet slot. In some embodiments, an air speed of approximately 35 miles per hour enables the collection of 5 μm particles on a selectable basis. For other embodiments, an air speed of 3.5 miles per hour generally selects for particles of 20 μm size. The dual air particle sample cassette 100 may use a snap fit clip or otherwise in order to obtain the snug fit between the top cover 102 and the bottom cover 104. The dual air particle sample cassette 100 forms a single, and possibly disposable unit for sampling the air particles in a predictable, reliable, and quantitative fashion. The cassette 100 enables the collection of two (2) air samples on a single collecting sheet 140. When the collecting sheet 140 is sent to the lab for handling and processing, both samples may be processed at the same time with very little risk of cross contamination between the two.

The top cover 102 is configured with two inlets 110, 112. The inlets are configured so that when a vacuum is drawn that pulls air through the narrow inlet slot 178, the tapering nature of the inlet creates significant air velocity at the narrow inlet slot 178 and past the sample plate 140. Various inlet configurations may be embodied in the cassette 100. Generally, air velocity determines the size of the particles that are sampled by the sample plate 140. The top cover 102 may have more then two inlets 110, 112. Indeed, configurations having three inlets, four inlets, or more may be possible. The rounded radial nature at the top 116 of the inlets 110, 112 may enable better air collection and sample results.

The central rib 172 separates the sample collecting areas into two or more compartments. Where more than two sample compartments 174 are present, additional ribs 172 may be required. Such ribs 172 prevent mixing or contamination between the multiple samples.

The bottom cover, or base, 104 has a single exit port 152 in the form of a vacuum nozzle 152. The use of a single vacuum source for both or all samples enables both concurrent sampling or sampling via one inlet and one sample compartment 174 at a time.

The dual air particle sample cassette 100 may collect and evaluate airborne fungi including viable and nonviable spores. The tacky material on the collecting slide 140 below the slit 178 may be present for nonviable sampling. A filter media can be used for viable sampling. A sticky filter media can be used for both viable and nonviable sampling.

Such filter media may include a variety of thin filters that optionally have an underlying support media. Some filter media may not require supporting substrates or the like to function well. In FIG. 3, a hybrid sample plate/collecting slide 140 is shown where the right side 190 of the slide 140 may be glass or some other flat surface that can be temporarily fixed to the top cover 102 via adhesive 192 present along the central rib 172. On the left side 194 of FIG. 3, filter media is shown that, instead of allowing air to pass around the filter media 196, the air or other gas passes through the filter media 196 and any particulate matter (according to the selection size of the filter media 196) is trapped in the filter media 196.

The filter media 196 may be any of a variety of materials in which particles above certain size may be trapped while particles below a certain size are allowed to pass through. In this way, a variety of filters can be constructed that selectively trap particles of certain sizes. The filter media should be sufficiently thin so that it fits within the spacing support ledge 176 of the bottom 130 of the top cover 102. The plenum space 198 generally between the sample plate 140 and the bottom 156 of the bottom cover 104 should be left open for the free and clear travel of air or other fluid there through.

The filter media 196 may have a backing or substrate 200 that may provide support to the primary filter media 196. The backing or substrate 200 may be made of paper or other porous but generally stiff material so that air or other fluid may pass through, yet the substrate 200 may not generally act as a filter media itself. In this regard, the substrate 200 should then have a collection size (that is a sufficiently porous structure) such that the substrate 200 serves to collect only particles that are larger, and not smaller, than those particles collected by the primary filter media 196.

The filter media 196 may also be a thin plastic film which is borne upon a substrate like paper, measure plastic or otherwise that selectively traps or holds back particles above a certain size. Whether the filter media 196 is a thin plastic film, a paper or fiber based filter material, or otherwise, the filter media 196 is permeable or porous to allow fluid and/or airflow through it yet selectively captures particles according to size on the filter membrane. The filter media may be used in conjunction with or in the place of a glass slide, sticky media or otherwise with respect to the sample plate 140.

Note should be taken, that the sample plate 140 generally does not in any way contact any of the side ledges, supports, and/or spacers 154 that intermittently circumscribe the perimeter of the bottom 156 of the bottom cover 104. This is to prevent any compression upon the slide 140 or to otherwise have the bottom cover 104 interfere with the operation of the sample plate 140.

Sample plate 140 is generally retained along the central rib 172 by adhesive 192 which is generally adhesive enough to provide stability for the sample plate 140 yet allows removal of the sample plate 140 from the top cover 102 to analyze the sample taken by the sample plate 140. The spacing support ledges 176 serve to help position and stabilize the sample plate 140. To provide additional stability and to direct airflow for filter media 196 sample plates 140, the gaps 142 shown in FIGS. 4 and 5 may be omitted with the filter media spanning the entire width of the bottom 130 of the top cover 102. This forces all air or other fluid through the filter media 196 to ensure collection of as much particulate matter as possible.

In such a case, the junction between the filter media 196 as a part of a sample plate 140 and the spacing support ledge 176 would be complete as shown in FIG. 3 around the entire perimeter of the filter media sample plate 140.

The collecting slide 140 may be temporarily fixed with a tacky material to the center cross support rib 172. The collecting slide 140 may be coded (as, for example, with etched letters "A" and "B") to uniquely correspond to similarly marked inlets ("A" and "B") in order to permanently identify the samples.

As partially shown in Figures, four or possibly more side ledges 154 extend upwardly from the base 104. Note should be taken that the sample plate 140 does not rest in any way upon the ledges 154. Instead, the central posts 136 as well as the circumscribing sidewall 132 are the portions of the top cover 102 which engage such ledges 154. In fact, generally, these are the only structures that do engage the side ledges 154.

The presence of the central rib 172 with its adhesive 192 enables the cassette 100 to be used in conjunction with a variety of different sample plates 140. While the cassette 100 may be disposable in nature, its useful life may extend far beyond that of a single use (or a divided single use if each of the two inlets 110, 112 are used at separate times).

By selecting an advantageous adhesive, a variety of sample plates 140 in the form of glass slides, plates, filter media, combinations thereof and the like of a variety of collection sizes and characteristics may be used to good effect. Advantageous selection of the adhesive 192 enables the detachable attachment of the sample plate 140 to the central rib 172. The spacing support ledges 176 of the top cover 102 then serve to provide lateral support for the sample plate 140 which would otherwise be able to rock back and forth much like a seesaw or teeter-totter about the central rib 172. The spacing support ledges 176 eliminate this degree of freedom for the sample plate 140 and prevents any rocking about the axis defined by the central rib 172. The central rib 172 itself prevents any rocking motion along an axis perpendicular to the central rib 172.

While multiple uses of the cassette 100 may require separate applications of adhesive 192, such applications are not seen as providing any significant contamination for the cassette should it be used in an otherwise clean environment. Under some circumstances, a pristine cassette 100 may be desirable and the cassette 100 may be subject to only a single use.

A disposable filter screen may be used in conjunction with the cassette 100 including filter screens with selectable openings ranging from 5 μm to 300 μm. Such a disposable filter screen may be fitted onto an inlet or fitted onto a separate attachment such as a collection hose for transmission of air samples to the cassette 100. Filtration prevents large particles and debris from entering the selected inlet and it also allows for particles of a known size only to be sampled.

The integrity of the samples gathered by the sample plate 140 may be maintained by using plastic caps fitted onto the inlet 110, 112 and exit 152 ports. This keeps an unused cassette clean prior to sampling and when one side is in use, the other sample chamber is protected from contamination or inadvertent use. Furthermore, the plastic caps prevent a used cassette from being contaminated after a sample has been collected.

Figure 6:
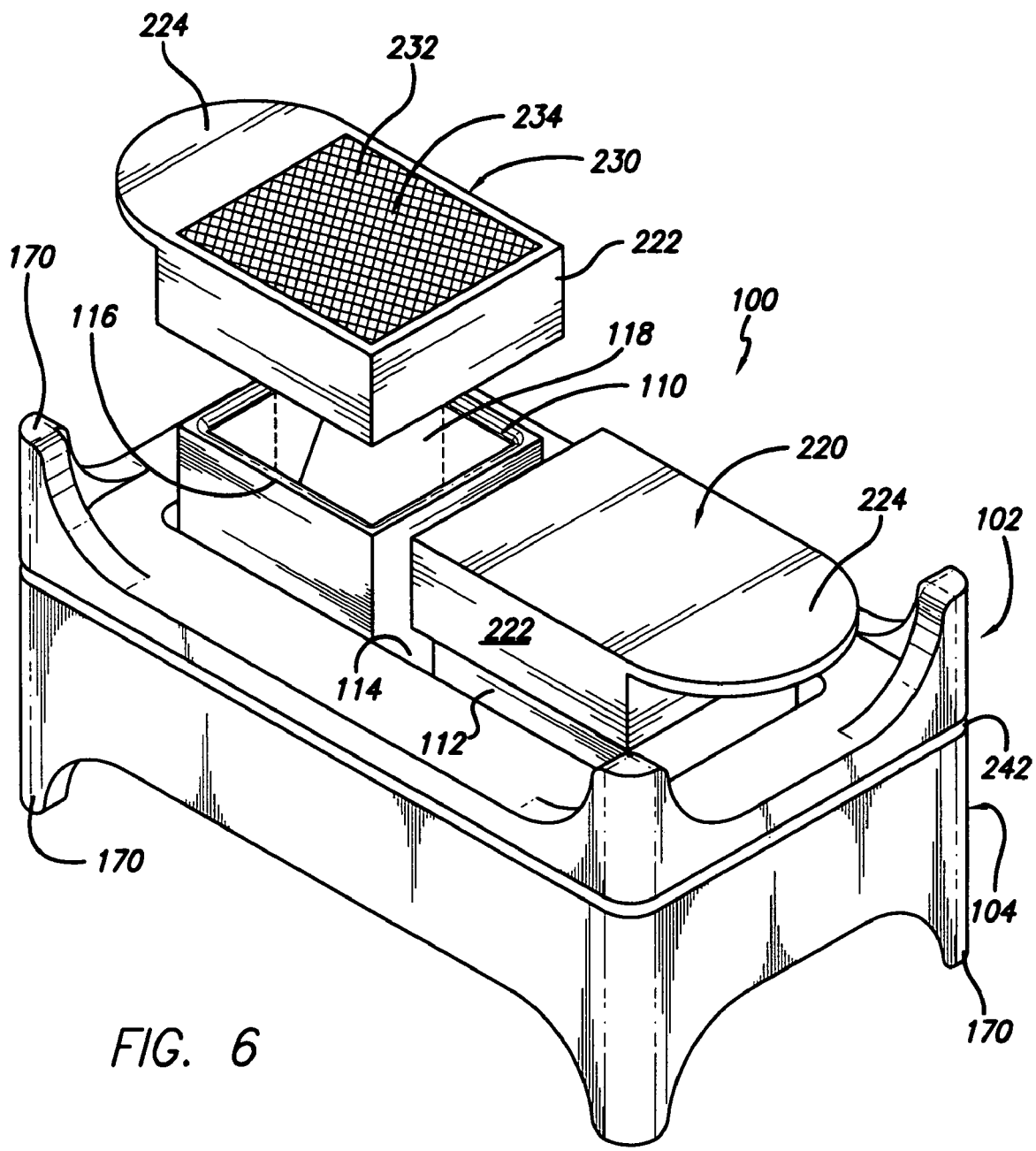
FIG. 6 is a side perspective view of the dual air particle sample cassette of FIG. 2 with a filter cap in a raised position and a regular cap in a fitted position.
Figure 7:
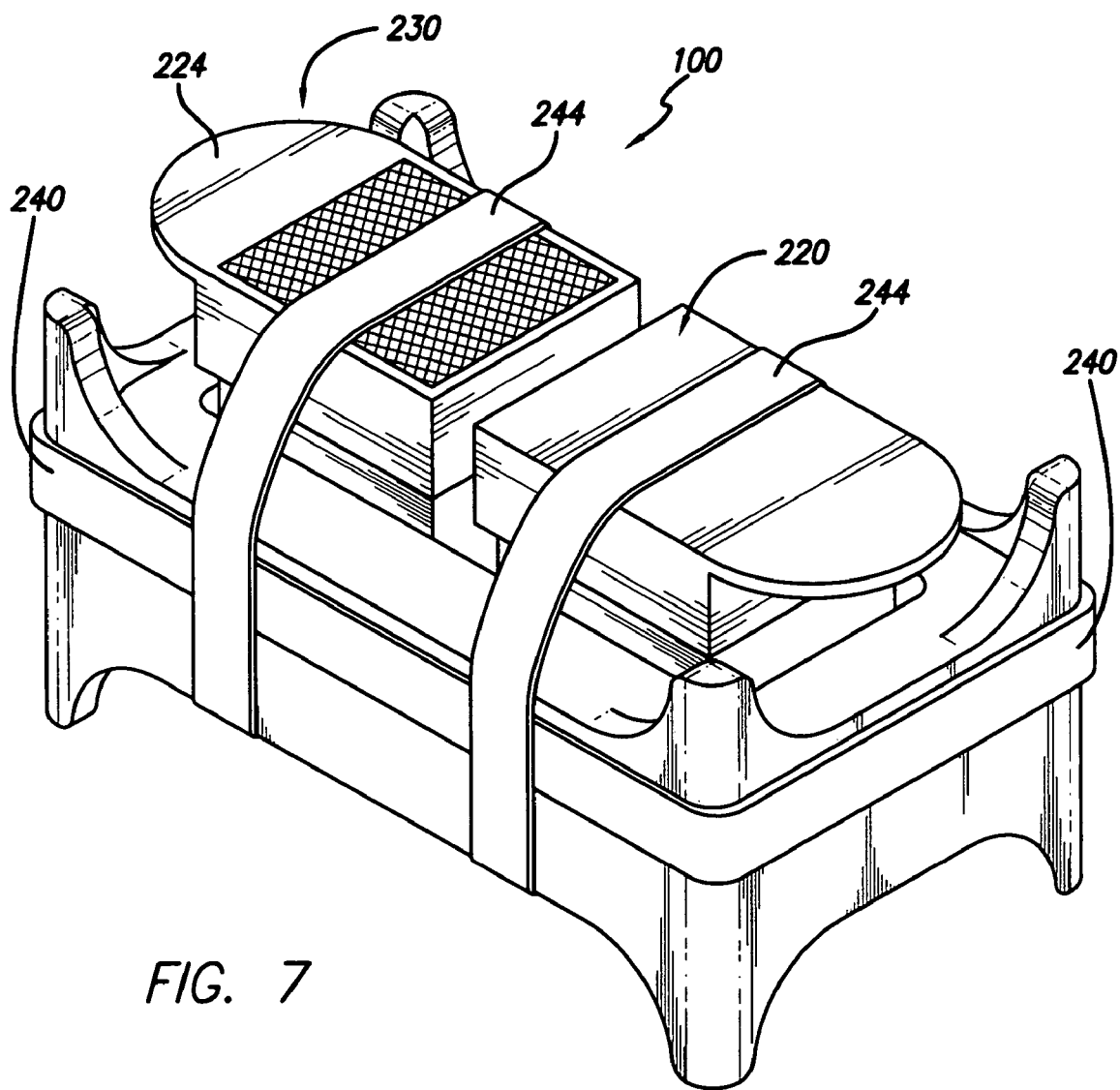
FIG. 7 is a side perspective view of the dual air particle cassette of FIG. 6 with both caps fitted and the cassette sealed with tape.

As shown in FIGS. 6 and 7, caps of a variety of types and characteristic may be used.

In FIG. 6, a first flat and sealingly covering cap 220 is shown affixed to the top cover 102 on the right inlet 112. The closed cap 220 has circumscribing walls 222 that in a generally sealingly engaging manner cover the inlet 112 and prevent fluid or airflow past the cap 220 and into the interior 118 of the inlet 112. The gap 220 may have a tab 224 that allows for easy manual engagement of the cap 220, allowing it to be easily removed from and replaced on the inlet 112. The cap 220 may be made of polypropylene or other material and is preferably soft so that it sealingly engages the top 116 of the inlet 112.

Also in FIG. 6, a second type of cap, a filter cap 230, is shown that also has circumscribing walls 222 that generally sealingly engage the inlet 110 (as shown in FIG. 6) by sealingly engaging the inlet top 116 and preventing a passage of air or other fluid into the interior 118 of the inlet 110. Both types of caps can be of any shape and/or size The filter cap 230 may also have a tab 224 for lifting and replacing the cap 230 from and on the inlet 110. As shown in FIG. 6, the filter cap 230 has a top mesh 232 that allows for the passage of air into and through the cap 230. The top mesh holds in compression or otherwise filter media 234 that may be similar to or different from the filter media 196 used in the sample plate 140. The filter media 234 may be generally entrapped by a second mesh (not shown) that resides within the interior of the filter cap 230 below the filter.

The filter media may act as a pre-filter to exclude particles larger than a certain particle size that may be present in the surrounding area when collection is made of an air sample. The resulting air passing into the interior 118 of the inlet 110 is then pre-filtered to exclude such larger particles. If a filter media 196 is used in conjunction with or as the sample plate 140, such filter media 196 may collect particles of a smaller size, enabling even smaller particles to go through. As a result, it would be possible (for example) to exclude sawdust in a dusty sawmill but still sample the air for pollen or the like as sawdust particles are generally very large while pollen particles would be able to pass through the filter cap 230 with its top mesh 232, through the filter media 234 and onto the sample plate 140.

If the sample plate is a glass slide with or without sticky media, the air flowing past the sample plate 140 would also be sampled for its particulate matter. Due to the nature of the sticky or other media, different materials or particles according to different sizes may be collected. Operation of the inlets 110, 112 with respect to the selection of particle size may generally not be affected by the presence or absence of a filter cap 230.

In FIG. 7, the capped dual air particle sample cassette 100 of FIG. 6 is shown in a sealed condition of the type normally presented to the end user of the cassette. Circumscribing tape 240 circumscribes the seam 242 (FIG. 6) present between the top cover 102 and the bottom cover 104 of the cassette 100. Lateral tapes 244 hold in place and maintain the seal provided by the caps 220, 234 in the example shown in FIG. 7. In order to seal the filter cap 230, a thin plastic or other obstructing sheet may be present underneath the lateral tape 244 holding the filter cap 230 in place. The sealing sheet (not shown) serves to seal the top mesh 232 and prevent air with its accompanying particulate matter from entering into the filter cap 230 past the top mesh 232.

Both types of tape, the circumscribing tape 240 for the seal 242 and the lateral tapes 244 for the caps 220, 230 are sufficiently adhesive and resilient to preserve the seals necessary so that samples cassettes 100 are not contaminated by inadvertent introduction of unintended particulate matter. The adhesive attachment of the tapes 240, 244 may be such that they may be removed generally without leaving any adhesive residue on the cassette 100. This prevents contamination of samples by adhesive material and generally allows the clean removal of the tapes 240, 244.

The lateral tapes 244 enable the selective use of either one of the inlets 110, 112 individually, or allow them to be used simultaneously. For the exemplary embodiment shown in FIG. 7, removal of the lateral tapes 244 and removal of the closed cap 220 as well as removal of any sealing sheet for the top mesh 232 of the filter cap 230 would enable two samples to be taken of the same fluid, or air, with the filter cap 230 pre-filtering such a sample to collect the smaller particles while the other side of the sample plate 140 corresponding to inlet 112 would receive all of the suspended particulate matter as such air was not pre-filtered. Under such circumstances, it may be advantageous to collect the filter media 234 of the filter cap 230 to subject it to testing.

The circumscribing seam sealing tape 240 may be removed upon delivery of the cassette 100 to a laboratory or other testing facility so that the sample plate 140 may be collected and analyzed.

While the present invention has been described with regards to particular embodiments, it is recognized that additional variations of the present invention may be devised without departing from the inventive concept.

What is claimed is:

1. An air particle sample cassette to sample air, comprising:
    a first cover having a plurality of inlets, each of said inlets having a tapering cross section with a first opening wider than a generally opposed second opening;
    each of said second openings leading to a recessed area within said cassette, said recessed area being defined by sidewalls and a rib, and being capable of receiving a sample plate;
    said rib separating at least two of said second openings and preventing gas flow therebetween when said sample plate is positioned over said recessed area; and
    a second cover removably enclosing said recessed area, said second cover defining a vacuum aperture; whereby when a vacuum is applied to said vacuum aperture, air is pulled through at least one of said second openings to encounter said sample plate, with matter in said air being collected by said sample plate as said air travels to said vacuum aperture.

2. An air particle sample cassette to sample air as set forth in claim 1, wherein one of said sidewalls establishes a gap with said sample plate when said sample plate is positioned over said recessed area, to direct said air about said sample plate before said air travels out of said vacuum aperture.

3. An air particle sample cassette to sample air as set forth in claim 1, wherein one of said sidewalls abuts said sample plate when said sample plate is positioned over said recessed area, to direct said air through said sample plate before said air travels out of said vacuum aperture.

4. An air particle sample cassette to sample air as set forth in claim 1, wherein said first cover defines a channel between said plurality of inlets and a perimeter of said first cover.

5. An air particle sample cassette to sample air as set forth in claim 1, wherein at least two of said plurality of inlets are separated from one another by a channel disposed in said cassette.

6. An air particle sample cassette to sample air as set forth in claim 1, wherein at least one of said inlets has flat exterior sides and a tapered top adjacent to a corresponding first opening.

7. An air particle sample cassette to sample air as set forth in claim 1, wherein at least one of said inlets is adapted to receive a cap adjacent to its first opening.

8. An air particle sample cassette to sample air as set forth in claim 1, wherein said sidewalls are partially discontinuous and extend past said sample plate so as to provide a seat for said sample plate and to protect said sample plate from contact with said bottom cover.

9. An air particle sample cassette to sample air as set forth in claim 1, wherein said bottom cover has side ledges for engaging said sidewall, said side ledges defining gaps at corners of said bottom cover through which air may flow to said vacuum aperture.

10. An air particle sample cassette to sample air as set forth in claim 1, and further comprising:
    said sample plate being removable and at least partially covered with an adhesive that retains said matter.

11. An air particle sample cassette to sample air as set forth in claim 1, and further comprising:
    a sample plate including materials selected from the group consisting of:
        tacky material, filter media, sticky filter media, non-viable sampling materials, and viable sampling materials.

12. An air particle sample cassette to sample air as set forth in claim 11, and further comprising:
    said tacky material being grease.

13. An air particle sample cassette to sample air, comprising:
    a top cover;
    said top cover having first and second aligned inlets, each inlet having a tapering cross section with a first opening wider than a generally opposed second opening;
    said first and second inlets each having generally flat exterior sides and a top adjacent to a corresponding first opening, each of said inlets being adapted to receive a cap adjacent to their respective first openings;
    said top cover defining a circumscribing channel between said first and second inlets and a perimeter of said top cover;
    said first and second inlets being separated from one another by a dividing channel;
    a removable sample plate including materials selected from the group consisting of:
        tacky material, grease, filter media, sticky filter media, non-viable sampling materials, and viable sampling materials;
    the second opening of each of said first and second inlets leading to a recessed area defined by sidewalls and a rib, said recessed area receiving said sample plate;
    said rib separating the second openings of each of said first and second inlets, and preventing gas flow therebetween as said sample plate is positioned over said recessed area;
    a bottom cover removably enclosing said recessed area, said bottom cover defining a vacuum aperture;
    said bottom cover having side ledges for engaging said sidewall, said side ledges defining gaps at corners of said bottom cover through which air may flow to said vacuum aperture; and
    said sidewalls being partially discontinuous and extending past said sample plate so as to provide a seat for said sample plate and to protect said sample plate from contact with said bottom cover including said side ledges; whereby
    when a vacuum is applied to said vacuum aperture, air is pulled through at least one of said second openings to encounter said sample plate, with matter in said air being collected by said sample plate as said air travels to said vacuum aperture.

14. An air particle sample cassette to sample air as set forth in claim 13, wherein one of said sidewalls establishes a gap with said sample plate when said sample plate is positioned over said recessed area, to direct said air about said sample plate before said air travels out of said vacuum aperture.

15. An air particle sample cassette to sample air as set forth in claim 13, wherein one of said sidewalls abuts said sample plate when said sample plate is positioned over said recessed area, to direct said air through said sample plate before said air travels out of said vacuum aperture.

16. An air particle sampling device, comprising:
    a cassette having a first inlet and a second inlet;
    a rib disposed within said cassette between said first and second inlets; and
    a sample plate removably attached by an adhesive to said rib.

17. An air particle sampling device as set forth in claim 16, wherein said sample plate is disposed proximate to said first and second inlets and said rib prevents transmission of air thereacross to isolate samples taken through said first and second inlets.

18. An air particle sampling device as set forth in claim 16, wherein said sample plate includes collection media selected from the group comprising:
tacky material, filter media, sticky filter media, non-viable sampling materials, and viable sampling materials.

19. An air particle sampling device as set forth in claim 18, wherein said tacky material comprises grease.

20. An air particle sampling device as set forth in claim 18, wherein said tacky material comprises grease.

21. An air particle sampling device as set forth in claim 16, wherein said sample plate is offset from said first and second inlets by said rib.

22. An air particle sampling device as set forth in claim 16, wherein said sample plate is offset from said first and second inlets by said rib.

* * * * *